United States Patent [19]

Weymuller, Jr.

[11] Patent Number: 5,033,466

[45] Date of Patent: Jul. 23, 1991

[54] DOBLE-CUFFED ENDOTRACHEAL TUBE

[76] Inventor: Ernest Weymuller, Jr., Harborview Medical Ctr., 325 Ninth Ave., Seattle, Wash. 98104

[21] Appl. No.: 540,315

[22] Filed: Jun. 19, 1990

Related U.S. Application Data

[63] Continuation of Ser. No. 316,819, Feb. 28, 1989, abandoned.

[51] Int. Cl.⁵ ............................................. A61M 16/00
[52] U.S. Cl. .......................... 128/207.15; 128/207.14; 128/200.26
[58] Field of Search ............... 128/207.14, 207.15, 128/200.26, 207.16, 207.18, 207.29

[56] References Cited

U.S. PATENT DOCUMENTS

| | | | |
|---|---|---|---|
| 3,640,282 | 2/1972 | Kamen et al. | 128/207.15 |
| 4,091,816 | 5/1978 | Elam . | |
| 4,285,340 | 8/1981 | Gezari et al. | 128/207.15 |
| 4,341,210 | 7/1982 | Elam . | |
| 4,423,725 | 1/1984 | Baran et al. | 128/207.15 |
| 4,538,606 | 9/1985 | Whited | 128/207.15 |
| 4,700,700 | 10/1987 | Eliachar . | |

OTHER PUBLICATIONS

"Laryngeal (Injury From Prolonged Endotracheal Intubation", The Laryngoscope Supplement No. 45–vol. 98, Part 2, Aug. 1988.

Primary Examiner—Aaron J. Lewis
Attorney, Agent, or Firm—Rockey and Rifkin

[57] ABSTRACT

An improved double-cuffed endotracheal tube designed for insertion through the mouth of a patient to provide a passage for artificial respiration. The device includes an elongated flexible tube having proximal and distal end portions, the distal end portion designed for insertion into a patient and the proximal end portion capable of connection to an artificial respirator. The tube includes a lower inflatable-deflatable cuff located above the distal end portion and secured to and encircling the tube. When properly positioned and inflated, the lower cuff sealingly engages the inner wall of the trachea below the larynx and prevents secretions from traveling into the upper trachea or larynx. The tube also includes an upper inflatable-deflatable foam-filled cuff secured to and encircling the tube above the lower cuff. The upper cuff is located on the tube at a predetermined point for positioning in the larynx between the vocal cords and cricoarytenoid joint. When properly positioned, the upper cuff extends equal distances above and below the glottis, and upon expansion or inflation, engages the interior surfaces of the larynx, preventing contact of the tube with those surfaces. The upper foam-filled cuff is designed to provide a sufficiently large area of contact between the cuff and laryngeal tissues to evenly distribute the pressure exerted by the endotracheal tube throughout the cuff, and protects the laryngeal tissues from injuries commonly caused by prolonged intubation of conventional endotracheal tubes.

4 Claims, 1 Drawing Sheet

DOBLE-CUFFED ENDOTRACHEAL TUBE

This is a continuation of copending application Ser. No. 07/316,819 filed on Feb. 28, 1989, abandoned.

BACKGROUND OF THE INVENTION

This invention relates generally to endotracheal medical devices, and more particularly to an improved endotracheal tube designed to reduce the severity of injury to the larynx due to acute and chronic laryngeal intubation.

Endotracheal tubes have been used for over a century to prevent obstruction of the upper airway passage or to facilitate ventilation of unconscious or anesthetized patients. Such devices have traditionally consisted of a relatively pliable tube shaped for insertion through the oral or nasal passage into the trachea and capable of being connected to respirator for introduction of air into the lungs. After repeated use of the traditional devices, deficiencies in these designs, including the escape of air from the respirator through the oral and nasal passages, were recognized. New designs were proposed to eliminate or reduce such deficiencies. One such design includes an inflatable-deflatable bag-like structure or cuff around the exterior of the tube at the end inserted into the trachea and positioned such that, upon insertion, the cuff is located in the trachea several centimeters below the larynx. When the tube is in place, the cuff is inflated and forms an airtight seal between the tube and the tracheal wall preventing the escape of air being pumped from the respirator into the lungs.

In an attempt to improve on the single-cuff design, another endotracheal tube was developed utilizing two cuffs, an esophageal cuff and an oral cuff. When a tube of this design is inserted into a patient, the cuffs seal the esophagus, preventing the backflow of the contents of the stomach into the lungs, and also prevent the escape of air being pumped into the lungs from the respirator.

Such designs, as well as others, allowed for prolonged intubation of endotracheal tubes in patients for periods of time ranging from several days to two weeks or more. With longer intubation periods, however, additional problems with such designs were recognized. Such problems included damage to the trachea walls due to pressure exerted by the cuffs, which decreased the perfusion of blood in the capillaries of the tracheal mucosa, and resulted in tissue necrosis after prolonged intubation. Also, laryngeal disfunction, due to movement of the endotracheal tube and the resulting contact within the posterior endolarynx, especially at the arytenoids, the cricoarytenoid joint and the surrounding tissues, was been observed and documented in several patients exposed to prolonged intubation periods.

As these problems, and others, were recognized, attempts were made to develop improved endotracheal tubes. U.S. Pat. Nos. 4,091,816; 4,341,210; 4,538,606; and 4,700,700 disclose endotracheal tubes designed to eliminate one or more of the problems associated with the earlier designs. U.S. Pat. No. 4,091,816 to Elam discloses a double cuff endotracheal tube with a standard cuff mounted on the exterior of the tube near its distal end and a second cuff located above the first cuff. The cuffs are connected so that air pumped into one may be transferred to the other. When a tube of this design is positioned in a patient, the first cuff is located within the mid-trachea a few centimeters below the larynx and the second cuff lies a few centimeters above the larynx. This design is intended to avoid damage to the trachea by allowing for the transfer of air between the cuffs and alleviating overpressurization and also attempts to avoid damage to the larynx by locating the cuffs on either side of the larynx.

Another design by Elam, disclosed in U.S. Pat. No. 4,341,210, is a double-cuffed endotracheal tube in which at least the upper cuff is an inelastic inflatable-deflatable cuff. The upper cuff occupies the cavity defined by the wall of the pharynx and seals the opening defined by the superglottic structure of the glottis. The lower cuff, which may also be inelastic, rests in the trachea at or below the opening defined by the lower lateral surface of the larynx. The cuffs have separate means of inflation, and, when a tube of this design is properly positioned, and inflated, in a patient, the arrangement of the cuffs is intended to avoid the same problems as the original Elam device.

U.S. Pat. No. 4,538,606 to Whited discloses another double-cuffed endotracheal tube which further attempts to eliminate the problems associated with earlier designs. Whited discloses an endotracheal tube with a lower bag-like membrane or cuff and an upper cuff or membrane mounted on the exterior of the tube. When the tube is positioned in a patient, the lower membrane or cuff is located in the trachea and, once inflated, creates a seal between the tube and trachea wall. The upper cuff is located in a position to contact the cricoarytenoid joint, and when properly positioned and inflated, cushions the joint from contact with the tube and positions the tube adjacent to, or into engagement with, the vocal cords of the larynx. The upper membrane or cuff may extend only partially around the exterior circumference of the tube. This design is intended to eliminate or reduce the mechanical trauma to the cricoarytenoid joint caused by the motion of the tube within the posterior endolarynx.

U.S. Pat. No. 4,700,700 to Eliachar discloses a doublecuffed endotracheal tube which includes upper and lower inflatabledeflatable cuffs and separate inflation and deflation means. When positioned in a patient, the lower cuff is located a predetermined distance below the larynx and the upper cuff, which extends around a certain portion of the posterior part of the tube, is located above the larynx. When inflated, the lower cuff sealingly engages the inner wall of the trachea and the upper cuff engages the posterior portion of the pharynx to effect a central alignment of the tube relative to the larynx such that the tube is located away from the posterior portion of the larynx. Like the devices described above, this device is intended to eliminate or reduce damage to the larynx and trachea.

Additional studies have revealed that an improved design is still necessary to decrease or eliminate laryngeal injury resulting from intubation of endotracheal tubes. The effects of endotracheal intubation may be viewed in three phases: (1) the acute phase, which occurs in the initial twenty-four hours of intubation and during which time transmucosal injury is established; (2) the chronic phase, which is of variable duration (prolonged intubation of days to weeks) and during which time transmucosal injuries, including granulation tissue, ulceration, chondritis, and damage to the arytenoid cartilage and cricoarytenoid joint occur; and (3) the healing phase, which begins after the endotracheal tube is removed. Studies have revealed that if transmucosal injury in the acute phase can be prevented, then the sequence of infection, cartilage damage and injury to the cricoarytenoid joint and laryngeal tissues can be avoided.

When an endotracheal tube is inserted into a patient, the fundamental cause of transmucosal injury is the pressure exerted between the wall of the tube and the soft tissues of the larynx. Pressure exerted by the endotracheal tube occludes the flow of blood through the capillaries of the soft tissues, initiating an ischemic injury. If the time of intubation is brief, i.e., minutes to hours, this injury is superficial; however, prolonged intubation of even one day may result in ischemic injury which becomes transmucosal to the level of the arytenoid cartilage, the cricoarytenoid joint and the surrounding laryngeal tissues. Such injuries may result in permanent scarring to the cricoarytenoid joint and surrounding tissues, causing prolonged or permanent laryngeal dysfunction and potentially requiring a permanent tracheotomy.

As documented studies have shown, the pressure exerted by an endotracheal tube is generated in two ways. First, there is a posteriorly directed leading force from the flexion of the tube as it conforms to the anatomy of the airway. Secondly, the tube also eats a lateral force distending the glottis, a force which increases with the tube diameter. The most common type of injury from this laterally directed force is vocal process erosion. The laterally directed force or pressure is the primary cause of mucosal injury in the acute phase and transmucosal injuries to the arytenoid cartilage, the cricoarytenoid joint and surrounding tissues in the chronic phase.

It has been determined that an endotracheal tube which reduces the lateral pressure exerted on the soft tissues of the larynx is needed. The present invention has been developed in response to that need, and provides an improved double-cuffed endotracheal tube utilizing a cuff having a larger contact area within the larynx thereby reducing the pressure exerted at any one point and protecting the laryngeal mucosa from ischemic injury in both the acute and chronic phases of endotracheal intubation.

SUMMARY OF THE INVENTION

The present invention relates to a double-cuffed endotracheal tube designed for insertion through the mouth of a patient to provide a passage for artificial respiration. The device includes an elongated flexible air tube having proximal and distal end portions, the distal end portion designed for insertion into a patient and the proximal end portion capable of correction to an artificial respirator. A lower inflatable-deflatable baglike membrane or cuff is located near the distal portion of the tube and can be inflated, once the tube is properly inserted into a patient, to provide a seal between the tube and the trachea wall to prevent the air being pumped by the respirator from escaping through oral or nasal passages.

The endotracheal tube of the present invention also includes an upper inflatable-deflatable foam-filled cuff mounted on the exterior surface of the tube above the lower cuff and located in a position to contact and cushion the larynx when the tube is properly placed within the trachea. The foam-filled cuff is subjected to a negative pressure upon insertion to allow for ease of insertion, and then allowed to expand and return to atmospheric pressure. The cuff extends completely around the exterior circumference of the tube, and cushions the soft tissues of the larynx, including the arytenoid cartilage, the cricoarytenoid joint and the vocal cords, from direct contact with the endotracheal tube. Separate means for inflating and deflating each cuff are also provided.

When the improved endotracheal tube of the present invention is properly inserted into a patient, the foam-filled cuff is positioned in the larynx to lie between the vocal cords, with the cuff extending equal distances above and below the glottis. When inflated, the foam-filled cuff evenly distributes the pressure exerted by the endotracheal tube along the entire surface of the cuff and allows blood to continue to flow through the capillaries in the soft tissues of the larynx. As a result of this distribution of pressure, decreased capillary perfusion and ischemic injury, which usually occur during the first few hours of intubation, is avoided. By preventing ischemic injury in the acute phase, a lower incidence of transmucosal injury to the larynx in the chronic phase can be and has been observed.

It is therefore an object of this invention to provide an improved endotracheal tube which eliminates or at least reduces the occurrence of ischemic and transmucosal injuries to the larynx.

It is another object of this invention to provide an improved endotracheal tube capable of cushioning and protecting the larynx, including the arytenoid cartilage, the cricoarytenoid joint and the vocal cords, from injury due to endotracheal intubation.

It is a further object of this invention to provide an improved endotracheal tube capable of both sealing the trachea without damaging the tracheal walls and protecting the larynx from transmucosal injury.

DETAILED DESCRIPTION OF THE INVENTION

Figure 1:
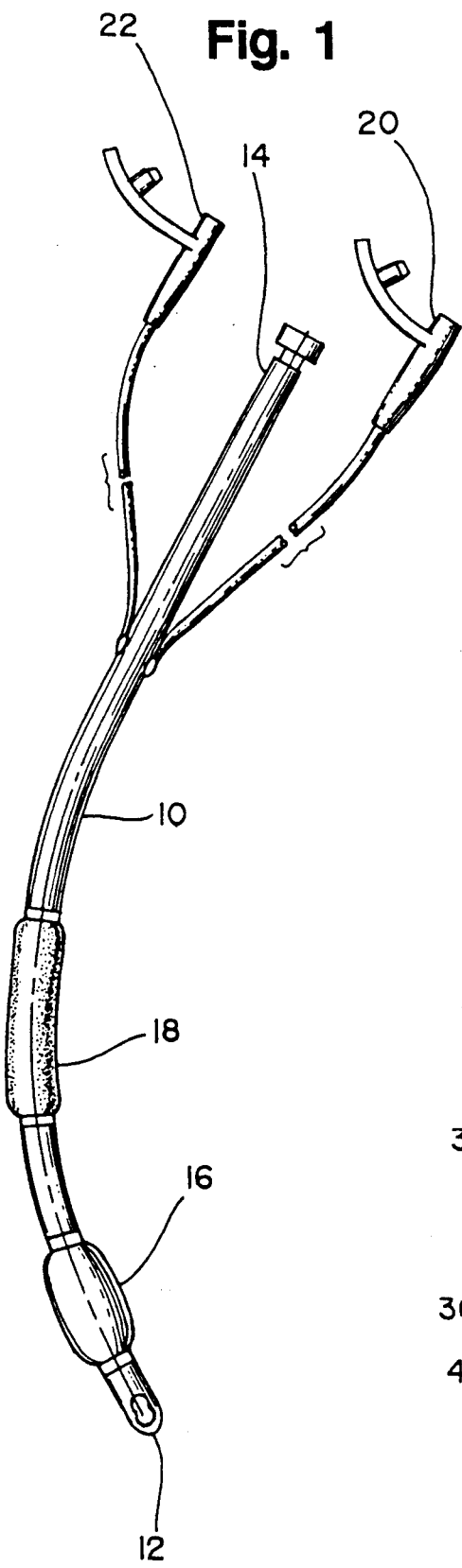
FIG. 1 is a perspective view of the improved endotracheal tube claimed herein.

Referring now to FIG. 1, the endotracheal tube of this invention includes an elongated flexible air tube 10 having a distal end portion 12 for insertion into a patient and a proximal end portion 14 capable of connection to a respirator (now shown). A pair of cuffs 16 and 18 encircle the tube 10 intermediate the proximal and distal end portions 12 and 14. The lower cuff 16 is located near the distal end portion 12 and is a bag-like membrane which can be inflated or deflated by means of a tube 20 connected to a source of air (not shown). The upper cuff 18 is a foam-filled cuff enveloped in a nonporous material and located a predetermined distance above the lower cuff 16. The upper cuff 18 can be inflated or deflated by means of a tube 22 connected to a source of air (now shown). The upper cuff 18 extends approximately 5 to 7 centimeters along the length of tube 10.

Figure 2:
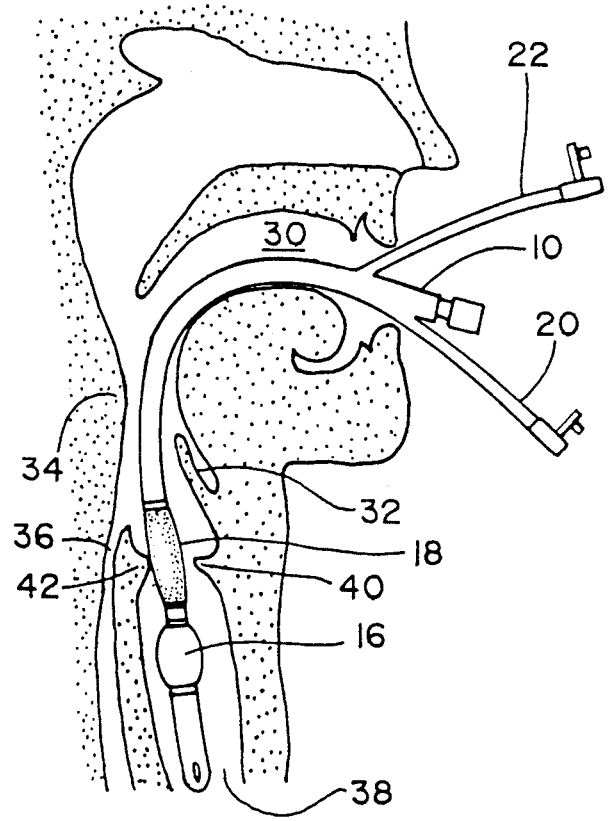
FIG. 2 is a partial cross-sectional, partial schematic view of the endotracheal tube inserted in a patient.
Figure 3:
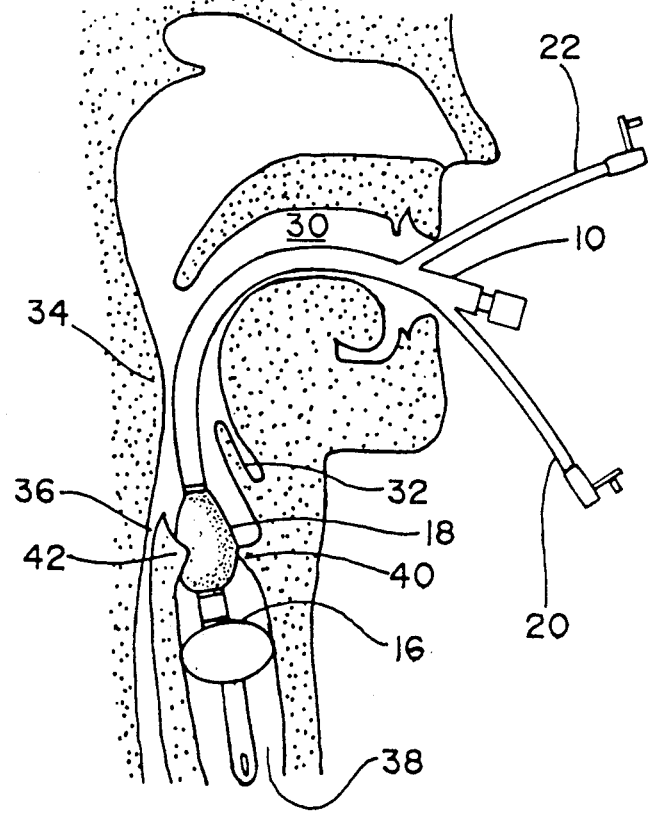
FIG. 3 is a partial cross-sectional, partial schematic view of the endotracheal tube installed and inflated in a patient.

The double-cuffed endotracheal tube 10 can be better understood by referring to FIGS. 2 and 3. As illustrated, the larynx 36 is a composite of the epiglottis 32, vocal cords 40 and the cricoarytenoid joint 42. The tube 10 is made from the same materials as many conventional endotracheal tubes and must be able to be inserted through the oral passage 30, past the epiglottis 32 and the posterior pharyngeal wall 34, and then through the larynx 36 so that the distal portion 12 of the tube 10 enters several centimeters into the trachea 38. When the tube 10 is properly positioned in a patient, the lower cuff 16 lies below the larynx 36 and in the trachea 38. As shown in FIG. 3, the cuff 16 is inflated with air to create a seal between the cuff 16 and the wall of the trachea 38 to anchor the tube 10 and also to prevent the escape of air being pumped through the tube 10 into the lungs. The pressure of the air inside cuff 16 should be sufficient to create a good seal between the cuff 16 and the walls of the trachea 38, but should be monitored to avoid the exertion of undue pressure on the walls of the trachea 38 which can damage the tissues by occluding blood flow.

As also illustrated in FIG. 2, the upper cuff 18 is located a few centimeters above the lower cuff 16 on tube 10. The upper cuff 16 consists of a foam-like material enveloped in silicone or other synthetic elastomers and is mounted to tube 10 by an adhesive or any other suitable means. When the tube 10 is inserted into a patient, negative pressure is applied through tube 22 to collapse cuff 18 for proper positioning in the patient. The cuff 18 should be positioned to lie between the vocal cords and the cricoarytenoid joint 42 in the larynx 36 with the cuff 18 extending an equal distance above and below the vocal cords 40. Radiopaque markers may be incorporated into cuff 18 to assure proper positioning. When the tube 10 is properly positioned, tube 22 is opened and cuff 18 expands until the pressure within the cuff 18 is equal to atmospheric pressure. As shown in FIG. 3, cuff 18 expands to contact the arytenoid cartilage, the cricoarytenoid joint and the surrounding tissues, and cushions the larynx from any direct contact with the endotracheal tube. If additional air is needed, tube 22 can be attached to an air supply to further expand cuff 18; however, the pressure should be monitored so that cuff 18 is not expanded to the point where the flow of blood through the tissues of the larynx decreases, causing ischemic injury to the laryngeal tissues.

As mentioned above, an important limitation of other endotracheal tube designs is the laryngeal injury associated with prolonged intubation. Laryngeal injury is caused by the contact of the endotracheal tubes with the arytenoid cartilage, the cricoarytenoid joint and the surrounding tissues. The pressure exerted by the endotracheal tubes on such tissues decreases the flow of blood through these tissues causing ischemic injury in the acute phase and transmucosal injury in the chronic phase of intubation. Also, such pressure on the cricoarytenoid joint can cause cricoarytenoid arthritis and permanent scarring in a number of patients.

The endotracheal tube of the present invention was developed to eliminate or at least reduce the cause of laryngeal injury and, particularly, the undue pressure exerted by the endotracheal tube on the tissues of the larynx. The foam-filled cuff 18 accomplishes this objective in at least two ways: first, it cushions the arytenoids, cricoarytenoid joint, surrounding tissues and vocal cords from the endotracheal tube; and secondly, it reduces the pressure exerted by the endotracheal tube at any given point in the larynx by increasing the area of contact between the cuff and the surrounding tissues. Therefore, by evenly distributing the pressure exerted by the endotracheal tube, the foam-filled cuff allows for the continuous flow of blood through the capillaries of the laryngeal tissues, preventing ischemic injury to the tissues, and also reduces the mechanical trauma caused by the endotracheal tube to the arytenoid cartilage, the cricoarytenoid joint and the vocal cords.

It is believed that prevention of ischemic injury, which occurs in the acute phase of endotracheal intubation, will eliminate or greatly reduce the sequence of infection, cartilage destruction and cricoid stenosis, which occurs in the chronic phase of intubation. Studies conducted on canine models support this belief.

Several animals were used in these studies, and were intubated with standard PVC endotracheal tubes of varying diameter and prototype tubes of the present invention. The periods of intubation ranged from 6 hours (acute phase) to 2 weeks (chronic phase) to 12 weeks. Examination of the laryngeal mucosa of the acute phase animals showed a visually obvious lesion left by the standard PVC tubes; there was no alteration of mucosal perfusion for the animals using the prototype of the present invention.

Studies conducted on the chronic phase animals show comparable results. All animals intubated for two weeks or more with the standard PVC tubes demonstrated mucosal ulceration and prominent granulation tissue in the posterolateral larynx. Destruction of the arytenoid cartilage was observed in some of the animals and others showed damage to the cricoarytenoid joint. As to the animals intubated with the prototype tube of the present invention, two experienced cuff failure due to damage to the cuff wall. In both these animals, the injuries were similar to the PVC tube animals, however, the cricoid cartilage was not injured. Other animals intubated with the prototype tube showed a thickened stratified squamous epithelium with a moderate underlying chronic inflammatory infiltrate. No ulceration or granulation tissue was present; the cartilage and cricoarytenoid joints were normal.

In view of the results of these studies, it is believed that the present invention overcomes the defects of conventional endotracheal tubes, both single-cuff and double-cuff devices. It will be understood by those skilled in the art that, while this invention has been described with reference to a preferred embodiment, various changes may be made without departing from the scope of the invention. Therefore, it is intended that the invention not be limited to the particular embodiment disclosed as the best mode contemplated for carrying out this invention, but that the invention will include all embodiments falling within the scope of the claims set forth below.

What is claimed is:

1. An endotracheal tube for insertion through the mouth and into the trachea of a patient to provide a passage for artificial respiration and (b) projection for the inner surfaces of the larynx during intubation comprising:

an elongated flexible air tube having a proximal end portion adapted to be located external to the mouth and a distal end portion adapted to be located within the trachea;

a lower inflatable-deflatable cuff secured to and located along said tube above the distal end portion of said tube for positioning in the trachea below the larynx, said cuff encircling said tube and operative upon inflation to sealingly engage the inner wall of said trachea below the larynx and prevent secretions from travelling into the upper trachea or larynx;

an upper inflatable-deflatable foam-filled cuff secured to said tube intermediate said proximal and distal end portions of said tube and located at a predetermined point on said tube for positioning said cuff in the larynx between the vocal cords and the cricoarytenoid joint upon intubation, said cuff encircling said tube and operative upon expansion or inflation to engage the interior surface of the larynx and prevent contact of said tube with said interior surfaces of the larynx, said cuff further being of sufficient length to extend above and below the larynx;

said upper inflatable-deflatable foam-filled cuff being capable of reducing the pressure exerted on the vocal cords, cricoarytenoid joint and other interior surfaces of the larynx by said endotracheal tube during intubation by distribution said pressure across the entire area of said cuff when said cuff is inflated or deflated to the desired pressure; and means for separating inflating and deflating said cuffs.

2. The endotracheal tube of claim 1 wherein said means of inflating and deflating said cuffs comprises separate channels within the wall of said tube extending from said cuffs to the proximal end portion of said tube.

3. The endotracheal tube of claim 2 wherein said upper inflatable-deflatable foam-filled cuff is deflated at the time of insertion by applying negative pressure through said inflation-deflation means and then inflated after positioning by removing said negative pressure and opening said channel, allowing said cuff to expand to and remain at atmospheric pressure.

4. The endotracheal tube of claim 1 wherein said upper inflatable-deflatable foam-filled cuff is approximately 5 to 7 centimeters in length.

* * * * *

UNITED STATES PATENT AND TRADEMARK OFFICE
CERTIFICATE OF CORRECTION

PATENT NO. : 5,033,466
DATED : July 23, 1991
INVENTOR(S) : Ernest A. Weymuller, Jr.

It is certified that error appears in the above-identified patent and that said Letters Patent is hereby corrected as shown below:

Column 6, line 50, add "(a)" after "provide";

Column 7, lines 3-4, "crici-oarytenoid" should be "crico-arytenoid";

Column 7, line 6, "surface" should be "surfaces"; and

Column 7, line 15, "distribution" should be "distributing".

Signed and Sealed this

Fifth Day of January, 1993

Attest:

DOUGLAS B. COMER

Attesting Officer     Acting Commissioner of Patents and Trademarks